United States Patent [19]

Shimazu et al.

[11] Patent Number: 4,906,572

[45] Date of Patent: Mar. 6, 1990

[54] METHOD OF CULTURING AMINO ACID RACEMASE-PRODUCING MICROORGANISM OF GENUS PSEUDOMONAS

[75] Inventors: Mitsunobu Shimazu; Fuzio Endo; Hideaki Yukawa, All of Ami, Japan

[73] Assignee: Research Association for Utilization of Light Oil, Tokyo, Japan

[21] Appl. No.: 21,356

[22] Filed: Mar. 3, 1987

[30] Foreign Application Priority Data

Mar. 3, 1986 [JP] Japan ................................ 41-44126

[51] Int. Cl.$^4$ ........................... C12N 9/90; C12R 1/40; C12R 1/38
[52] U.S. Cl. .................................... 435/233; 435/247; 435/253.3; 435/253.6; 435/877
[58] Field of Search ................... 435/233, 253.3, 253.6, 435/247, 877

[56] References Cited

U.S. PATENT DOCUMENTS 4,335,209 6/1982 Asai et al. .......................... 435/233
4,587,214 5/1986 Harada et al. ...................... 435/877
4,783,403 11/1988 Araki et al. ......................... 435/193

Primary Examiner—Robert A. Wax
Attorney, Agent, or Firm—Wenderoth, Lind & Ponack

[57] ABSTRACT

A method of culturing an amino acid racemaseproducing microorganism of the genus Pseudomonas, which comprising culturing said microorganism in a culture medium containing at least one compound selected from the group consisting of glycerol, ethanol, tartaric acid, fumaric acid and succinic acid as a carbon source, and recovering microorganism cells containing the amino acid racemase in an increased amount.

3 Claims, No Drawings

METHOD OF CULTURING AMINO ACID RACEMASE-PRODUCING MICROORGANISM OF GENUS PSEUDOMONAS

This invention relates to a method of culturing an amino acid racemase-producing microorganism of the genus Pseudomonas, and more specifically, to a method of increasing the harvest of amino acid racemase by culturing an amino acid racemase-producing microorganism of the genus Pseudomonas in a medium containing a specific carbon source.

Amino acids obtained by organic synthesis methods are usually in DL-form, and when one of these optical isomers L and D is desired, they must be separated, for example, by optical resolution. In this method, it is the usual practice to racemize the amino acids left after separation of the desired optical isomer, and recycle the resulting DL-form to the optical resolving step.

In the production of L-amino acids such as L-cysteine, L-tyrosine and L-tryptophan by an enzymatic method using DL-serine as a substrate, the unreacted D-serine builds up in the reaction system. In an industrial operation, the unreacted D-serine is recovered and racemized, and recycled to the reaction step.

Thus, in the field of amino acid production, effective utilization of DL-amino acids that can be produced at relatively low costs by an organic synthesis method frequently requires a racemization step. Heat-treatment and enzymatic racemization have previously been known as the method of racemizing amino acids. The heat-treatment method, however, is not industrially advantageous because the desired amino acids are thermally decomposed and their yields and purities are reduced. The enzymatic method is an industrially good method because it can be carried out by a reaction at room temperature under normal atmospheric pressure and no decomposition of the desired amino acids occurs.

Amino acid racemase produced by Pseudomonas putida (IFO 12996) is a typical example of an enzyme which catalyzes racemization of amino acids (i.e., amino acid racemase). The amino acid racemase produced by Pseudomonas putida is inert to aromatic amino acids and amino acids in which the beta-methyl group is substituted, such as isoleucine, valine and threonine, but are active on many other amino acids such as lysine, arginine, methionine, alanine and serine and have the excellent ability to racemize these amino acids [see Biochemical and Biophysical Research Communication, Vol. 35, No. 3, 363–368 (1969); "Seikagaku (Biochemistry)", Vol. 46, No. 5, 203–2232 (1974)].

The amount of the above amino acid racemase produced by Pseudomonas putida, however, is very small and insufficient for using the enzyme on an industrial scale. In an attempt to increase the harvest of amino acid racemase by Pseudomonas putida, a method was previously proposed which comprises culturing the above microorganism while glucose is continuously or intermittently added so that the concentration of glucose in the culture medium is maintained at not more than 1% (see Japanese Laid-Open Patent Publication No. 20187/1983). This method is based on the finding that the production of the above enzyme is inhibited when glucose is used as a carbon source. However, so long as glucose is used as a carbon source, the problem of the inhibited production of the enzyme cannot be basically obviated to whatever extent the concentration of glucose in the culture medium is lowered, and the harvest of the enzyme is difficult to increase greatly by this method. Furthermore, an extra device is required for controlling the glucose concentration in the culture medium to not more than 1%, and the operation becomes complex and is industrially disadvantageous.

With the foregoing background, the present inventors made various investigations on the method of increasing the productivity of amino acid racemase by Pseudomonas putida without using glucose as a carbon source. These investigations have led to the discovery that when culturing is carried out using glycerol, ethanol, tartaric acid, fumaric acid or succinic acid as a carbon source, the productivity of amino acid racemase is markedly increased.

According to this invention, there is provided a method of culturing an amino acid racemase-producing microorganism of the genus Pseudomonas, which comprising culturing said microorganism in a culture medium containing at least one compound selected from the group consisting of glycerol, ethanol, tartaric acid, fumaric acid and succinic acid as a carbon source, and recovering microorganism cells containing the amino acid racemase in an increased amount.

The microorganism which can be used in the method of this invention belongs to the genus Pseudomonas and has the ability to produce amino acid racemase. A preferred specific example is Pseudomonas putida deposited under number 12996 in Institute for Fermentation, Osaka (IFO) at 2-17-85, Jusohonmachi, Yodogawa-ku, Osaka-fu, Japan and being freely available from this depository. Other amino acid racemase-producing microorganisms of the genus Pseudomonas may also be used in this invention.

The characteristic feature of the method of this invention is that the microorganism is cultured in a medium containing at least one compound selected from the group consisting of glycerol, ethanol, tartaric acid, fumaric acid and succinic acid as a carbon source. Glycerol, ethanol and tartaric acid are preferred, and glycerol is the most preferred carbon source.

The amount of the carbon source can be varied depending upon its type. Generally, it is desirable to use the carbon source in such an amount that its total concentration in the medium during the culturing is at least 0.5% (w/v). The upper limit of its amount is not strictly set. Usually, the upper limit is from 10 to 50% (w/v) varying depending upon the type of the carbon source. The preferred concentration of the carbon source in the medium at the start of culturing is 0.5 to 20% (w/v) for glycerol, 0.5 to 5% (w/v) for ethanol, 0.5 to 20% (w/v) for tartaric acid, 0.5 to 20% (w/v) for fumaric acid, and 0.5 to 20% (w/v) for succinic acid. When two or more carbon sources are used together, the concentration of each of them may be within the above range.

The carbon source may be added to the medium at a time at the start of culturing, or may be added portionwise during the period of culturing.

In the method of this invention, other carbon sources need not to be used together with the above-specified carbon source. If required, however, an organic nutrient source which can be a carbon source, such as yeast extract, polypeptone, corn steep liquor, meat extract and Casamino acid may be used in a small proportion, preferably in an amount 1/5 or less, more preferably 1/10 or less, of the amount of the above-specified carbon source.

The amino acid racemase-producing microorganism of the genus Pseudomonas may be cultured in a culture medium known per se under culture conditions known per se, for example by using the culture medium containing nitrogen sources or inorganic substances and the culture conditions which are described in the literature references described above. Examples of the nitrogen sources in the culture medium used in the present invention include ammonium salts such as ammonium sulfate, ammonium chloride and ammonium phosphate; ammonia; nitrates such as potassium nitrate, sodium nitrate and ammonium nitrate; and organic nitrogen compounds such as glutamic acid, glutamine, aspartic acid and asparagine. Examples of the inorganic substances include potassium phosphate, magnesium sulfate, sulfates and hydrochlorides of iron, manganese, zinc, cobalt and calcium. Growth promoting substances may be incorporated in the culture medium. Examples include vitamins such as thiamine and biotin; amino acids such as methionine and cysteine; and yeast extract, polypeptone, meat extract, corn steep liquor and Casamino acid which contain the foregoing substances partly or wholly. Nutrient sources other than the carbon sources may be added in sufficient amounts to the culture medium as in the prior art.

The culturing temperature is generally 10 to 45° C., preferably 25 to 40° C. The pH of the culture medium is generally 3 to 10, preferably 5 to 9. During the culturing, the pH of the medium is desirably maintained constant within the above range by adding ammonia, sodium hydroxide, potassium hydroxide, etc.

The culturing is carried out under aerobic conditions, and the culture medium is desirably aerated and agitated so that the dissolved oxygen may not become a rate controlling factor during the culturing.

The period of culture varies depending upon the carbon source and the culture conditions, but is generally 4 hours to 3 days.

According to the method of this invention, the use of the specific carbon source can greatly increase the productivity and harvest of the amino acid racemase, as demonstrated by Examples given hereinbelow. The cells cultured by the method of this invention are recovered from the culture medium by a method known per se, and may be used directly as wet or dry cells in the racemization reaction. Alternatively, they may be used after they are subjected to a crushing treatment. It is also possible to separate the amino acid racemase from the cells, and use the separated racemase.

The following Examples illustrate the method of this invention in greater detail.

EXAMPLE 1

A 500 ml Erlenmeyer flask was charged with a 100 ml aliquot of a culture medium (pH 7.2) consisting of 10 g of polypeptone, 10 g of meat extract, 5 g of NaCl and 1000 ml of distilled water, and the medium was sterilized at 120° C. for 15 minutes. One platinum loopful of Pseudomonas putida (IFO 12996), an amino racemase-producing microorganism, was inoculated in the medium, and pre-cultured at 30° C. for 15 hours. One milliliter of the culture was inoculated in 100 ml of a culture medium having the composition shown in Table 1, and cultured at 30° C. for 20 hours.

The cells were collected from 40 ml of the culture fluid by centrifugation (6,000 rpm, 15 min., 4° C.). The collected cells were washed once with 40 ml of 0.1M phosphate buffer (pH 8.0), and suspended in 4 ml of the buffer. The cell suspension was crushed by an ultrasonic crusher (Model 200 BRANSON), and then centrifuged (12,000 rpm, 40 min., 4° C.). The supernanant was separated as a crude enzyme solution, and then stored in the refrigerated state at -20° C. for 24 hours in order to inhibit the serine decomposing activity of the crude enzyme solution.

TABLE 1

| | |
|---|---|
| $K_2HPO_4$ | 7 g |
| $KH_2PO_4$ | 2 g |
| $(NH_4)_2SO_4$ | 1 g |
| $MgSO_4.7H_2O$ | 0.1 g |
| Tryptone (Difco) | 1 g |
| Carbon source (*) | 15 g |
| Distilled water | 1000 ml |
| pH 7.0 | |

(*) The carbon source was one of glycerol, ethanol, fumaric acid, succinic acid, tartaric and glucose.

The resulting crude enzyme solution (0.5 ml) was added to 4.5 ml of an aqueous reaction solution (pH 8.0) containing the compounds shown in Table 2, and reacted at 37 ° C. for 30 minutes. The change of the specific rotation of serine in the reaction solution was measured under acidic conditions using a polarimeter (Model D1P360 of Nippon Bunko K.K.). The total serine concentration was measured by HPLC, and the amount of L-serine formed from D-serine was determined. The amount of proteins in the crude enzyme solution was determined by the method of Lowry et al. [J. Biol. Chem., 193, 265 (1951)]. Using these data, the activity of the enzyme per unit amount of proteins was calculated. The results are shown in Table 3 in which the activities are expressed by relative values taking the activity of the enzyme obtained in the case of using glycerol as a carbon source as 100.

TABLE 2

| |
|---|
| 100 mM tris(hydroxymethylaminomethane), pH 8.0 |
| 100 mM D-serine |
| 0.04 mM pyridoxal-5-phosphoric acid |

TABLE 3

| Carbon source | Relative activity |
|---|---|
| Glycerol | 100 |
| Ethanol | 97 |
| Succinic acid | 70 |
| Fumaric acid | 71 |
| Tartaric acid | 90 |
| Glucose (control) | 35 |

EXAMPLE 2

Example 1 was repeated except that L-methionine was used instead of D-serine shown in Table 2. The results are shown in Table 4 as in Example 1.

TABLE 4

| Carbon source | Relative activity |
|---|---|
| Glycerol | 100 |
| Ethanol | 98 |
| Succinic acid | 75 |
| Fumaric acid | 73 |
| Tartaric acid | 89 |
| Glucose (control) | 36 |

EXAMPLE 3

Example 1 was repeated except that L-lysine hydrochloride was used instead of D-serine shown in Table 2. The results are shown in Table 5 as in Example 1.

TABLE 5

| Carbon source | Relative activity |
| --- | --- |
| Glycerol | 100 |
| Ethanol | 100 |
| Succinic acid | 79 |
| Fumaric acid | 75 |
| Tartaric acid | 98 |
| Glucose (control) | 33 |

EXAMPLE 4

A 100 ml aliquot of a culture medium (pH 7.2) composed of 10 g of polypeptone, 10 g of extract, 5 g of NaCl and 1,000 ml of distilled water was poured into a 500 ml Erlenmeyer flask, and sterilized at 120° C. for 15 minutes. Pseudomonas putida (IFO 12996), an amino acid racemase-producing microorganism, was inoculated in the medium, and pre-cultured at 30° C. for 15 hours. Two milliliters of the culture was inoculated in 100 ml of the same culture medium as above, and cultured at 30° C. for 15 hours.

The culture was inoculated in 1 liter of a culture medium having the composition shown in Table 6 in a two-liter jar fermentor (made by Iwashiya), and cultured at 30° C. for 24 hours with aeration and agitation at 600 rpm and 1 v/v/m. As required, the pH of the culture medium was adjusted to a constant value of about 7.2 by adding 25–28% ammonia.

TABLE 6

| | |
| --- | --- |
| $K_2HPO_4$ | 7 g |
| $KH_2PO_4$ | 2 g |
| $(NH_4)_2SO_4$ | 1 g |
| $MgSO_4.7H_2O$ | 0.1 g |
| Tryptone | 1 g |
| Yeast extract | 1 g |
| Glycerol | 20 g |
| pH 7.0 | |

Ten milliliters of the culture was centrifuged (6,000 rpm, 15 minutes, 4° C.) to collect the cells. The cells were washed once with 40 ml of 0.1M phosphate buffer (pH 8.0), and suspended in 2 ml of the same buffer. The cell suspension was crushed by an ultrasonic crusher (Model 200 BRANSON) and centrifuged (12,000 rpm, 40 minutes, 4° C.). The supernatant was separated as a crude enzyme solution. To inhibit the serine decomposing activity of the crude enzyme solution, it was stored in the refrigerated state at $-20°$ C. for 24 hours.

The racemase activity on serine was measured by the same operation as in Example 1.

As a control, the above procedure was repeated except that glucose was used as the carbon source. The results are shown in Table 7.

TABLE 7

| Carbon source | Glycerol | Glucose |
| --- | --- | --- |
| Amount of the cells yielded (g.dry.cell/l) | 7.5 | 7.0 |
| Relative activity | 100 | 35 |

What is claimed is:

1. A method for producing an amino acid racemase which comprises culturing Pseudomonas putida IFO 12996 in a culture medium therefor containing at least one compound selected from the group consisting of glycerol, ethanol and tartaric acid as carbon source,, the total concentration of the carbon source added to the medium during the culturing being at least 0.5% (w/v), and recovering from the medium microorganism cells containing the amino acid racemase.

2. The method of claim 1 wherein the carbon source is gylcerol and the concentration in the medium at the start of culture is 0.5 to 20% (w/v).

3. The method of claim 1 wherein the carbon source is at least one compound selected from the group consisting of glycerol and ethanol and the concentration of the carbon source in the medium at the start of culturing is 0.5 to 20% (w/v) for glycerol and 0.5 to 5% (w/v) for ethanol, and when two carbon sources are used together, the concentration of each of them is within said range.

* * * * *

UNITED STATES PATENT AND TRADEMARK OFFICE
CERTIFICATE OF CORRECTION

PATENT NO. : 4,906,572
DATED : March 6, 1990
INVENTOR(S) : MITSUNOBU SHIMAZU, FUZIO ENDO and HIDEAKI YUKAWA It is certified that error appears in the above-identified patent and that said Letters Patent is hereby corrected as shown below:

On the title page, in section [30] Foreign Application Priority Data, change "41-44126" to read --61-44122--.

Signed and Sealed this

Tenth Day of September, 1991

Attest:

HARRY F. MANBECK, JR.

*Attesting Officer*  *Commissioner of Patents and Trademarks*